(12) United States Patent
Gurskis

(10) Patent No.: US 9,254,190 B2
(45) Date of Patent: Feb. 9, 2016

(54) TOOLS, SYSTEMS, AND METHODS FOR REMODELING TISSUE

(75) Inventor: Donnell W. Gurskis, Belmont, CA (US)

(73) Assignee: Medtronic, Inc., Minneapolis, MN (US)

( * ) Notice: Subject to any disclaimer, the term of this patent is extended or adjusted under 35 U.S.C. 154(b) by 631 days.

(21) Appl. No.: 13/613,333

(22) Filed: Sep. 13, 2012

(65) Prior Publication Data

US 2013/0110226 A1 May 2, 2013

Related U.S. Application Data

(63) Continuation of application No. 12/560,404, filed on Sep. 15, 2009, now abandoned.

(60) Provisional application No. 61/097,193, filed on Sep. 15, 2008.

(51) Int. Cl.
*A61F 2/24* (2006.01)
*A61B 17/00* (2006.01)

(52) U.S. Cl.
CPC .............. *A61F 2/2427* (2013.01); *A61F 2/2445* (2013.01); *A61F 2/2466* (2013.01); *A61B 2017/00783* (2013.01); *A61F 2250/001* (2013.01)

(58) Field of Classification Search
CPC ............... A61B 2017/00783; A61F 2250/001; A61F 2/2427; A61F 2/2445; A61F 2/2466

USPC ....................... 623/2.11, 2.36–2.38, 2.4, 2.41
See application file for complete search history.

(56) References Cited

U.S. PATENT DOCUMENTS

| 5,467,763 A | 11/1995 | McMahon et al. |
| 6,524,338 B1 | 2/2003 | Gundry |
| 6,962,605 B2 | 11/2005 | Cosgrove et al. |
| 6,989,028 B2 | 1/2006 | Lashinski et al. |
| 7,704,269 B2 * | 4/2010 | St. Goar et al. ............. 623/2.36 |
| 2004/0138744 A1 | 7/2004 | Lashinski |
| 2005/0171601 A1 | 8/2005 | Cosgrove |
| 2007/0233239 A1 | 10/2007 | Navia |

* cited by examiner

*Primary Examiner* — Julian W Woo

(57) ABSTRACT

A tool for remodeling a tissue annulus includes an elongate handle and a reshaping element on a distal end of the handle. The reshaping element may be directable between a first configuration to facilitate direction through a tissue annulus, and a second curved configuration to remodel tissue adjacent the tissue annulus. The tool may be used for treating a tissue annulus within a patient's heart, e.g., by introducing the reshaping element through the tissue annulus, and manipulating the tool to reshape the tissue annulus substantially to a contour of the reshaping element. The reshaping element may support the tissue while a prosthesis is secured to the tissue annulus, or the reshaping element may itself be secured to the tissue annulus and released from the tool.

22 Claims, 7 Drawing Sheets

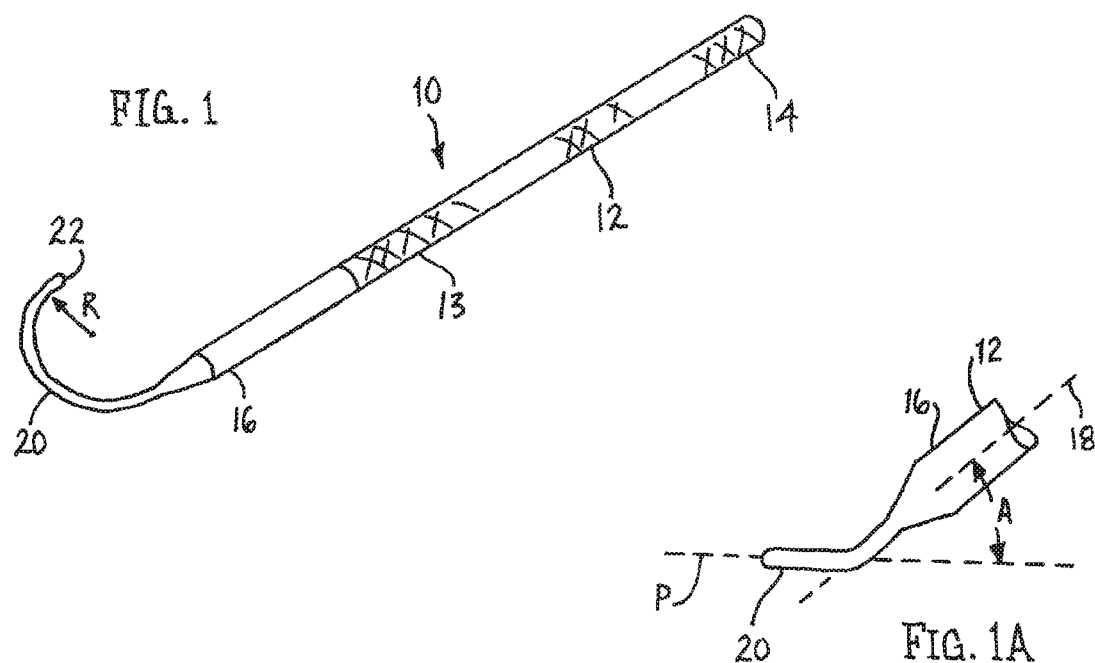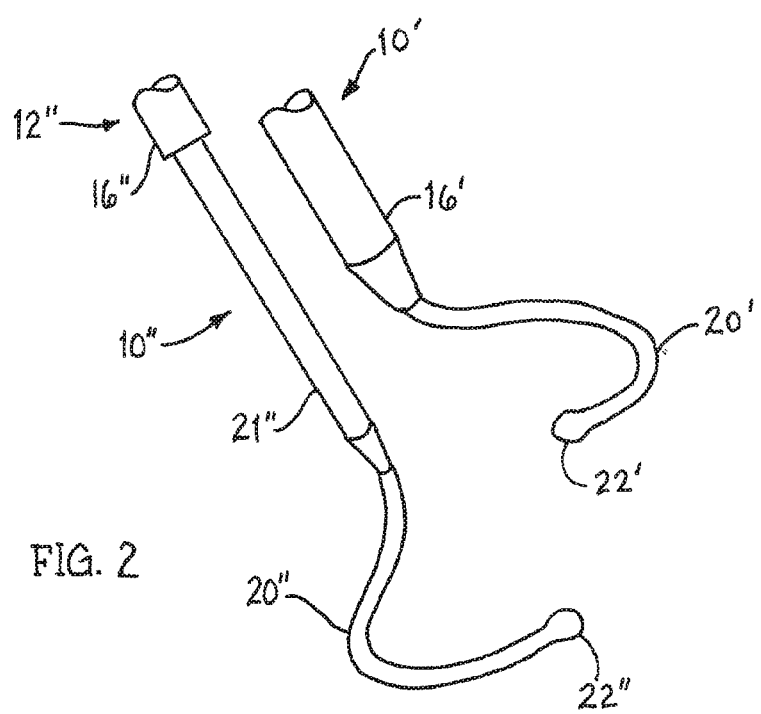

TOOLS, SYSTEMS, AND METHODS FOR REMODELING TISSUE

RELATED APPLICATION DATA

This application is a Continuation of and claims priority from U.S. patent application Ser. No. 12/560,404 filed Sep. 15, 2009, which claims benefit of provisional Ser. No. 61/097,193, filed Sep. 15, 2008, the entire disclosures of which are expressly incorporated by reference herein.

FIELD OF THE INVENTION

The present invention relates generally to tools, systems, and methods for remodeling tissue, for example, for reshaping, remodeling, or otherwise treating a tissue annulus, such as the mitral valve annulus.

BACKGROUND

Mitral valve repair generally involves introducing a prosthesis, e.g., using sutures, clips, and/or other fasteners, to secure and/or reshape the mitral annulus. The tools, systems, and methods disclosed herein may be used to temporarily or permanently reshape a tissue annulus, such as the mitral annulus.

SUMMARY

The present invention is directed to tools, systems, and methods for remodeling tissue, for example, for reshaping, remodeling, or otherwise treating a tissue annulus, such as the mitral valve annulus.

In accordance with one embodiment, a tool is provided for treating a tissue annulus that includes an elongate handle including a proximal end and a distal end; and a reshaping element on the distal end terminating in a distal tip and having a shape to remodel tissue adjacent a tissue annulus.

In one embodiment, the reshaping element is directable between a first configuration to facilitate direction through a tissue annulus, and a second curved configuration to remodel tissue adjacent the tissue annulus. In the second configuration, the reshaping element may define a portion of a circle, e.g., an arc having an angle less than ninety degrees. Alternatively, the reshaping element may have a more complicated curvilinear shape in the second configuration.

An actuator may be provided on the proximal end of the handle, e.g., coupled to the reshaping element for directing the reshaping element between the first and second configurations. In addition or alternatively, the actuator may allow the reshaping element to be released from the handle of the tool. For example, an actuator member may extend from the proximal end of the handle to the distal tip, and the actuator may be coupled to the actuator member for pulling or otherwise actuating the actuator member to cause the reshaping element to be directed from the first configuration to the second configuration.

In another embodiment, the reshaping element may be releasable from the handle, e.g., to provide an implant for supporting tissue adjacent a tissue annulus. In this embodiment, the reshaping element may be at least partially covered with fabric.

In accordance with another embodiment, a system is provided for treating a tissue annulus that includes one or more tools, each tool comprising an elongate handle including a proximal end and a distal end, and a reshaping element on the distal end terminating in a distal tip and having a shape to remodel tissue adjacent a tissue annulus. In addition, the system may include a plurality of fasteners receivable through tissue adjacent the tissue annulus, a tool for delivering fasteners into tissue adjacent the tissue annulus, and/or a prosthesis.

For example, the fasteners may be clips, such as elastic or superelastic clips that are provided initially in a relaxed configuration in which legs of the clips cross. During delivery, the clips may be directed to a constrained configuration, e.g., in which the legs are directed to a "U" shaped configuration, the legs may be directed through tissue surrounding the annulus, and the clip released, whereupon the clips resiliently return towards the relaxed configuration. Alternatively, the fasteners may include sutures, e.g., including needles on one or both ends for inserting the sutures through and/or tying the sutures to tissue, e.g., to secure a prosthesis relative to the tissue.

In one embodiment, the fasteners may be sized, shaped, and/or otherwise configured for securing the reshaping element on the tool to tissue adjacent the tissue annulus, and the reshaping element may be releasable from the handle.

In another embodiment, a prosthesis may be provided that is configured for supporting the tissue annulus, and fasteners may be receivable through the prosthesis for securing the prosthesis to tissue adjacent the tissue annulus. In exemplary embodiments, the prosthesis may have an annular shape, a "C" shape, or other shapes, e.g., to provide an annuloplasty ring for treating a mitral valve.

In accordance with still another embodiment, a method is provided for treating a tissue annulus within a patient's heart that includes introducing a distal end of a remodeling tool through the tissue annulus, and reshaping the tissue annulus substantially to a contour of the tool distal end.

In one embodiment, the tool distal end may be introduced through the tissue annulus in a first configuration, the tool distal end may be directed to a second curved configuration below the tissue annulus, and tissue adjacent the tissue annulus may be lifted, supported, or otherwise remodeled using the tool distal end in the second curved configuration.

Optionally, a prosthesis may be introduced into the patient's heart adjacent the tissue annulus, and secured to tissue adjacent the tissue annulus. Once the prosthesis is secured to the tissue, the tool distal end may be removed from the tissue annulus. The tool distal end may have a shape corresponding to the shape of the prosthesis to support tissue adjacent the tissue annulus while fasteners are delivered to secure the prosthesis to tissue adjacent the tissue annulus.

In another option, the tool distal end may be secured to tissue adjacent the tissue annulus, and then released from a handle of the tool such that the tool distal end provides a reshaping or support element that may remain implanted at the tissue annulus site indefinitely.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 1 is a perspective view of an exemplary embodiment of a tool for remodeling tissue including a movable reshaping element directed to a curved configuration.

FIG. 1A is a side view of the tool of FIG. 1.

FIG. 2 is a perspective view of a pair of tools including curved reshaping elements on distal ends thereof.

FIG. 4B1 is a detail of the reshaping element of FIG. 4B, showing connectors on the reshaping element for releasably attaching the reshaping element to the handle of FIG. 4A.

FIG. 4C1 is a detail of the reshaping element of FIG. 4C, showing a connector on the reshaping element for releasably attaching the reshaping element to the handle of FIG. 4A.

DETAILED DESCRIPTION OF THE EXEMPLARY EMBODIMENTS

Figure 3:
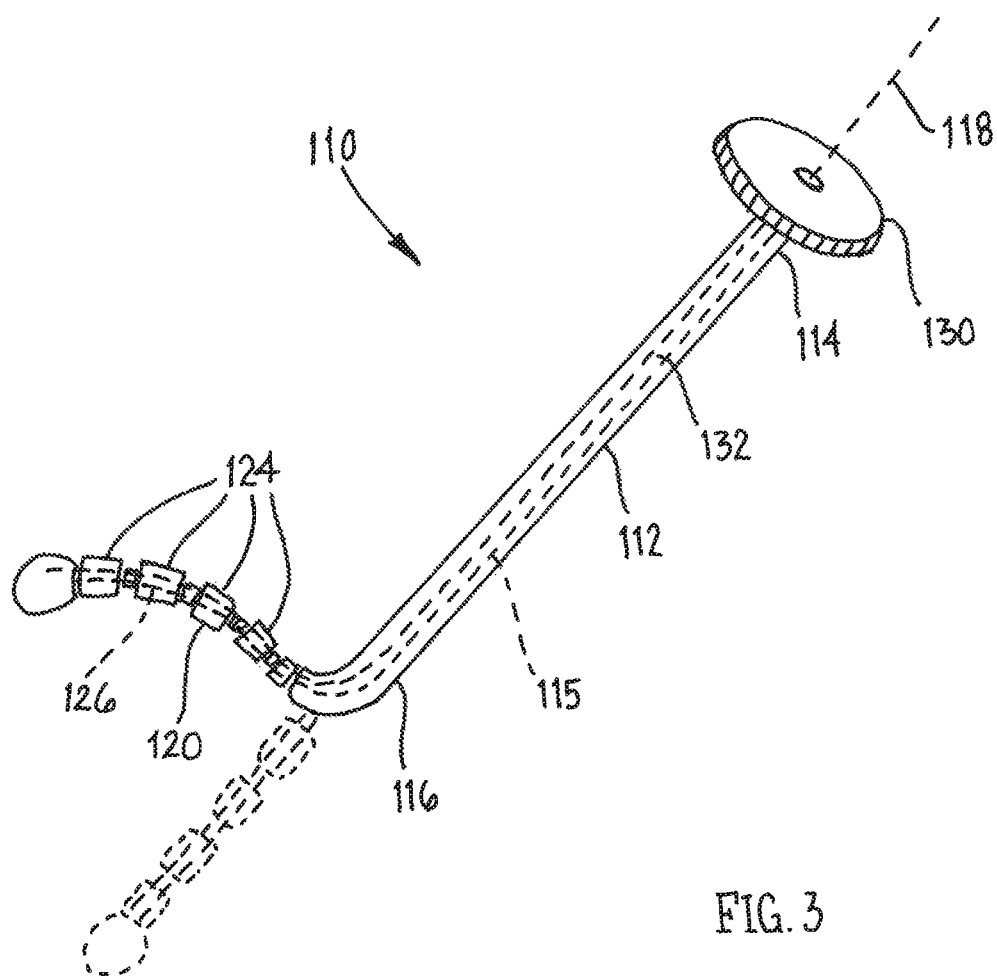
FIG. 3 is a perspective view of another exemplary embodiment of a tool for remodeling tissue including an actuator on a proximal end thereof for changing a shape of a reshaping element on a distal end thereof.

Turning to the drawings, FIG. 1 shows an exemplary embodiment of a tool 10 for remodeling tissue that generally includes an elongate handle 12 and a reshaping element 20 having a shape to remodel tissue adjacent a tissue annulus, such as a mitral valve annulus (not shown). Generally, the handle 12 is a substantially rigid elongate member, e.g., a solid or hollow shaft, including a proximal end 14 and a distal end 16 from which the reshaping element 20 extends. The handle 12 may have a length sufficient to introduce the reshaping element 20 into a target tissue region, e.g., a tissue annulus, from outside the patient's body, e.g., between about ten and forty centimeters (10-40 cm) or between about ten and twenty centimeters (10-20 cm).

Optionally, the handle 12 may include one or more features to facilitate manipulation of the tool 10 during use. For example, as shown in FIG. 1, the handle 12 may include knurling 13, ridges, or other raised or recessed features (not shown) along all or a portion of the handle 12 to facilitate gripping the tool 10 and reduce the risk of the handle 12 slipping, e.g., if exposed to blood or other fluids. In addition or alternatively, the handle 12 may include an enlarged handpiece (not shown) on the proximal end 14, e.g., having an ergonomic or other shape to facilitate gripping the tool 10 and/or including one or more actuators (also not shown) for manipulating features on the tool 10 (e.g., as described further below).

As shown in FIG. 1, the reshaping element 20 is integrally formed with the handle 12, e.g., extending from the distal end 16 and terminating in a distal tip 22 of the tool 10. For example, the handle 12 and reshaping element 20 may be integrally formed by machining from stock material using a lathe or other equipment, casting, injection molding, extruding, and the like. The tool 10 may be formed from metal, such as stainless steel, aluminum, titanium, and the like, plastic, or composite material having properties to provide a substantially rigid handle 12 and malleable (or alternatively substantially fixed) reshaping element 20. If desired, the material of the handle 12 and/or reshaping element 20 may be treated, e.g., to soften the material of the reshaping element 20 relative to the handle 12 to allow the reshaping element 20 to be plastically curved or otherwise shaped as desired.

Alternatively, as shown in FIG. 2, the handle 12" and reshaping element 20" may be formed separately and attached together, e.g., by interference fit, bonding with adhesive, cooperating connectors, and the like. In this alternative, the handle 12" and reshaping element 20" may be formed from different materials having desired rigidity and/or malleability. For example, the handle 12" may be formed from metal or plastic, while the reshaping element 20" may be formed from malleable metal. Optionally, in this alternative, a shaft portion 21" of the reshaping element 20" may be relatively rigid compared to the portion extending to the distal tip 22," e.g., such that the shaft portion 21" does not bend substantially when the reshaping element 20" is shaped or otherwise manipulated during use.

As shown in FIG. 1, the distal tip 22 may have rounded, atraumatic shape, e.g., to facilitate introducing the reshaping element 20 between tissue structures within a patient's body, such as between valve leaflets, chordae tendinae, and the like (not shown). Optionally, as shown in FIG. 2, the reshaping element 20' may include a relatively large, e.g., bulbous, distal tip 22' to further prevent risk of puncturing or otherwise damaging tissue during use of the tool 10.' The bulbous distal tip 22' may also facilitate manipulating tissue during use of the tool 10.'

Returning to FIG. 1, the reshaping element 20 may be malleable or otherwise plastically deformable, e.g., such that the reshaping element 20 may be manipulated into a desired shape that will be retained after such manipulation to provide a desired shape during use. Thus, a user may modify the shape of the reshaping element 20 based upon the anatomy encountered and/or to correspond to a shape of a prosthesis to be introduced into a tissue annulus. For example, as shown in FIG. 1, the handle 12 may have a larger diameter (or other cross-section) than the reshaping element 20, e.g., such that the handle 12 is substantially rigid while the reshaping element 20 is bendable. In an exemplary embodiment, the handle 12 may have a diameter (or other maximum cross-section) between about 0.5 and two centimeters (0.5-2.0 cm), while the reshaping element 20 may have a diameter (or other maximum cross-section) between about one and five millimeters (1.0-5.0 mm).

Alternatively, the reshaping element 20 may have a substantially fixed shape, e.g., defining a predetermined arc or other curvilinear shape. For example, as shown in FIG. 1A, the reshaping element 20 may curve within a plane "P" that intersects a longitudinal axis 18 of the handle 12, e.g., defining an angle "A" between the axis 18 and plane "P." In exemplary embodiments, the angle "A" may be between about ten and ninety degrees (10-90°), e.g., between about thirty and sixty degrees (30-60°), and the like. The reshaping element 20 may define an arc having a substantially fixed radius of curvature "R," as shown in FIG. 1, e.g., extending around an angle less than ninety degrees (90°), e.g., between about forty five and ninety degrees (45-90°). Alternatively, the reshaping element may have a varying radius of curvature along its length and/or more complicated curvilinear shape than a simple arc, if desired, based on the anatomy encountered. The length of the reshaping element 20 may be sufficient to define an arc length extending partially around a tissue annulus, e.g., having a length between about twenty and forty millimeters (20-40 mm).

In this alternative where the reshaping element 20 has a substantially fixed shape, it may be desirable to provide a set of tools, with each tool including one or more of a different angle "A," radius of curvature, arc length, and the like than the others. Thus, a user may select an appropriate tool from the set based on the particular anatomy encountered during a procedure. The tools may be intended for single use, or may be reusable, e.g., such that the tool(s) may be sterilized after use and used during a subsequent procedure on another patient.

Figure 5:
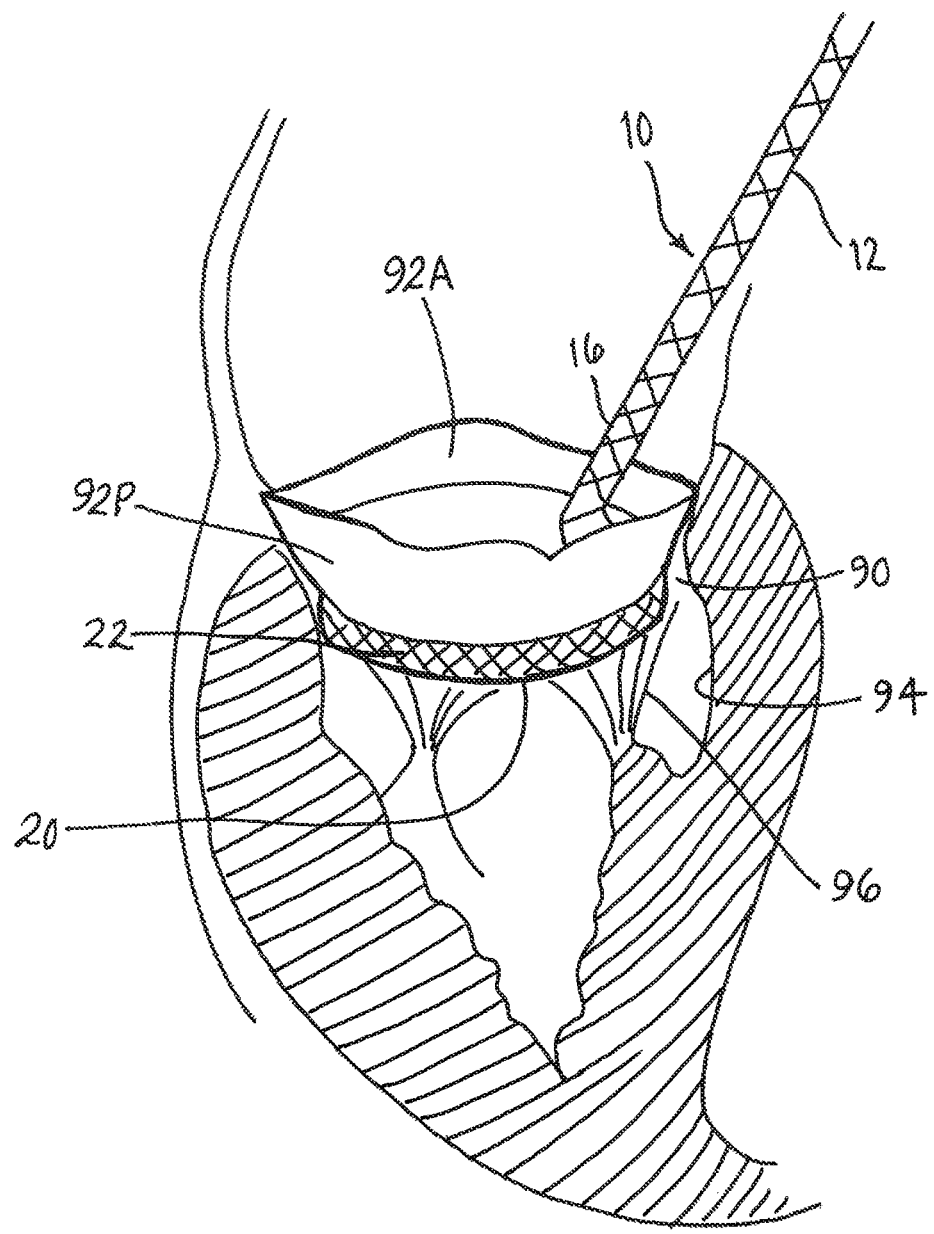
FIG. 5 is a perspective view of a portion of a patient's heart showing a tool remodeling tissue adjacent a mitral annulus.

Turning to FIG. 5, the tool 10 of FIG. 1 is shown placed through a mitral valve annulus 90 of a heart, e.g., between leaflets 92 and/or around other valve structures, such as the chordae tendinae 96 and the ventricular wall 94. The tool 10 may be introduced into a patient's body using a sternotomy, thoracotomy, port, or other access method to gain access to the valve annulus 90 being treated, e.g., under direct visualization. The distal tip 22 may be passed through the leaflets 92 and the reshaping element 20 may be threaded behind the leaflets 92 and chordae tendinae 96, as shown in FIG. 5. The handle 12 may then be manipulated, e.g., to lift or otherwise reshape the tissue of the valve annulus 90 for treatment. If the reshaping element 20 is malleable, at any time, the shape may be changed based on the anatomy encountered. Thus, if the reshaping element 20 is introduced into the valve annulus 90 but does not provide a desired remodeled shape, the tool 10 may be removed, the reshaping element 20 adjusted and the tool reintroduced. Alternatively, if the reshaping element 20 is substantially fixed, the tool 10 may be removed and another tool with a different, desired reshaping element (not shown) may be introduced instead and used to remodel the tissue.

Figure 6:
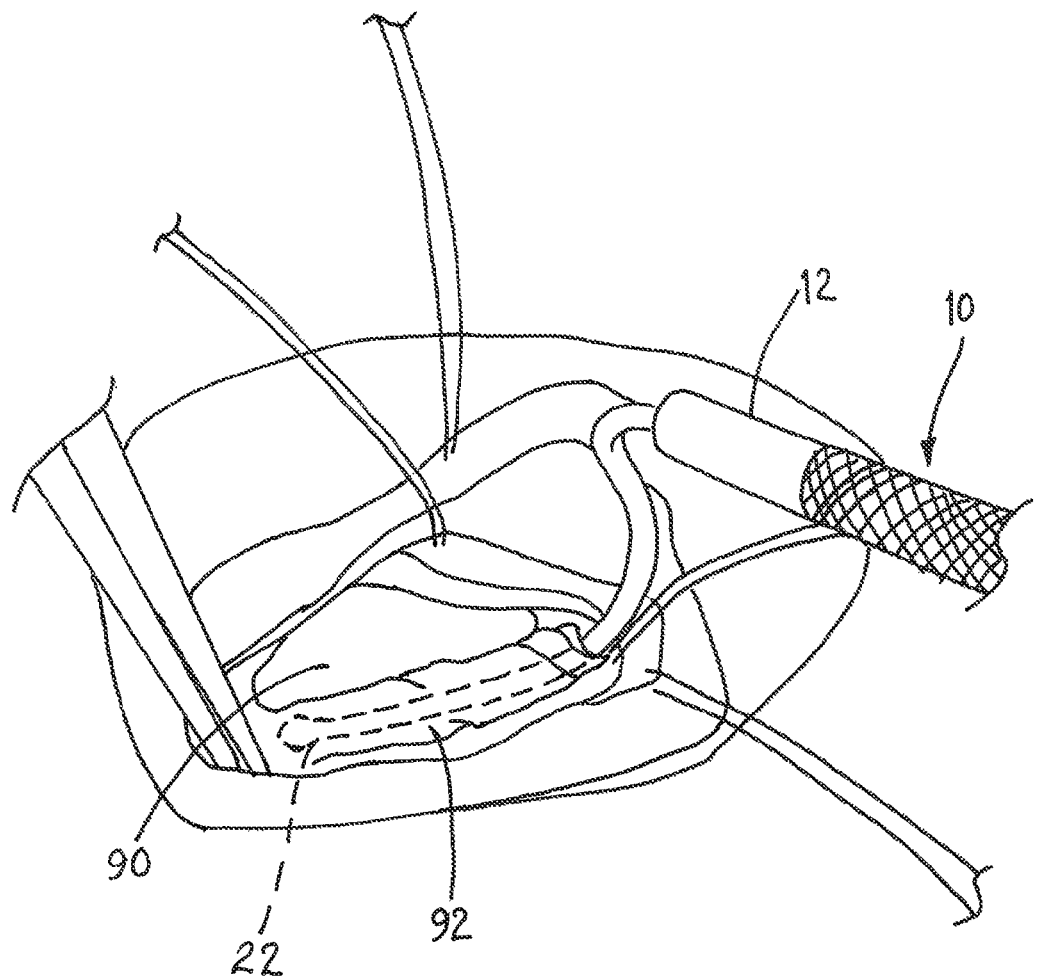
FIGS. 6-8 are perspective views of a patient's heart showing a method for treating a mitral valve annulus that includes remodeling tissue adjacent the valve annulus using a tool and delivering fasteners through a prosthesis into tissue adjacent the valve annulus to secure the prosthesis to the tissue while a tool remodels the tissue.
Figure 7:
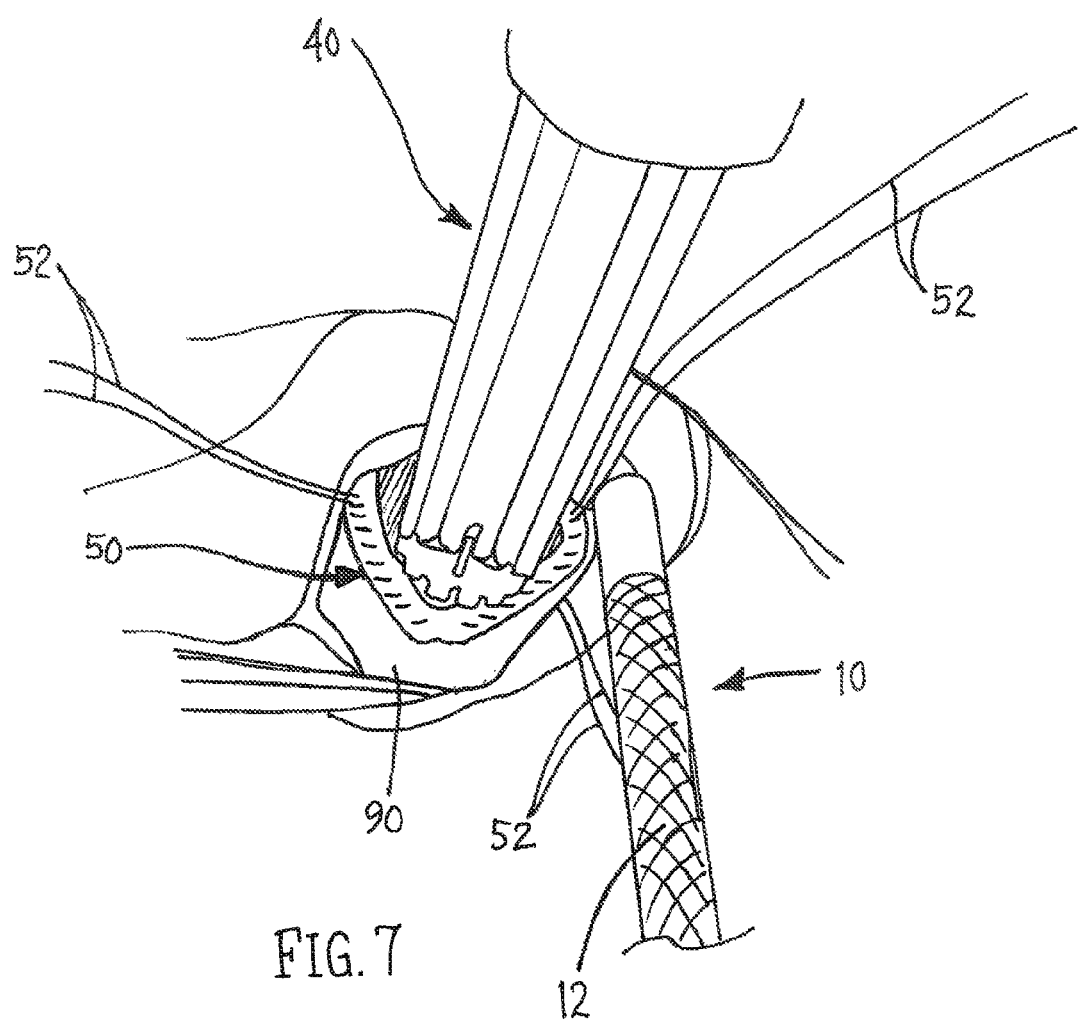
Figure 8:
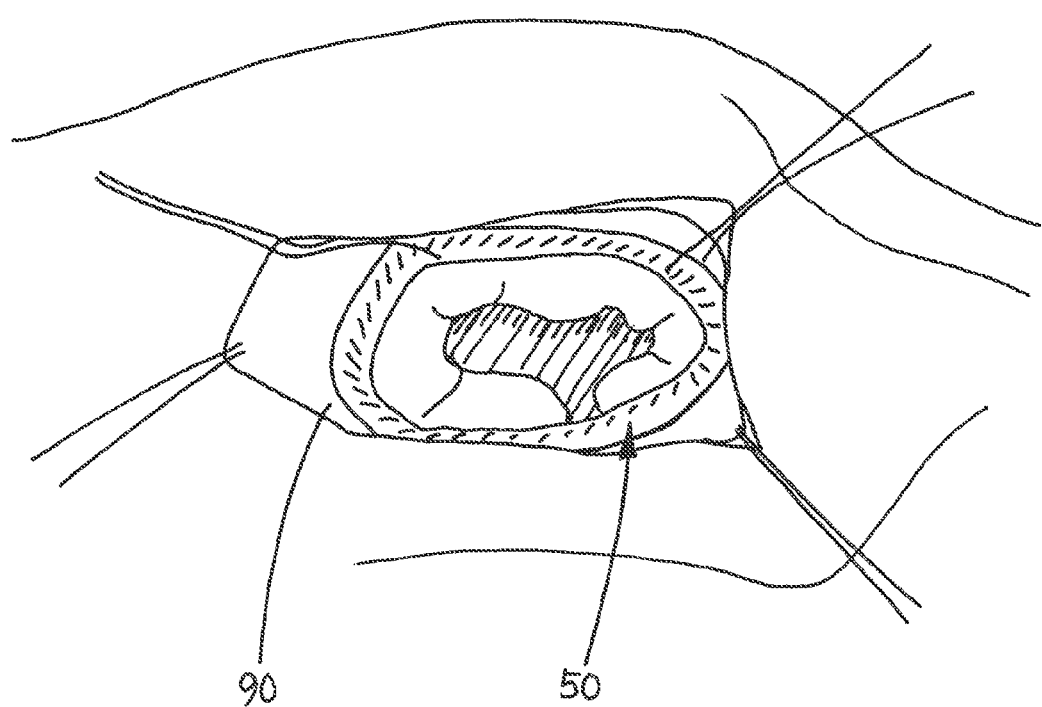

In an exemplary method, shown in FIGS. 6-8, the tool 10 (or set of tools) may be provided in a kit or system, e.g., including one or more additional components. For example, as shown in FIGS. 7 and 8, a kit or system for treating a valve annulus may include one or more tools 10 (one shown), a fastener tool 40 for delivering a plurality of clips or other fasteners (not shown), and a prosthesis 50, such as an annuloplasty ring. Optionally, the kit or system may also include one or more forceps, sutures, needles, and the like.

Initially, as shown in FIG. 6, the reshaping element 22 of tool 10 may be introduced through the tissue annulus 90, i.e., through the valve leaflets 92 and below the tissue surrounding the tissue annulus 90, e.g., as described above with reference to FIG. 5. Optionally, one tool may be introduced to support each of the existing valve leaflets (not shown). For example, as shown in FIG. 2, a first tool 10' may include a reshaping element 20' that curves in a clockwise direction (viewed from the proximal end) and a second tool 10" may include a reshaping element 20" that curves in a counterclockwise direction. Thus, each reshaping element 20', 20" may be introduced through the tissue annulus 90 and placed under respective leaflets. The tool(s) may be manipulated to support and/or remodel the tissue surrounding the tissue annulus 90, e.g., to correspond to the shape and/or facilitate apposition of a prosthesis 50 intended for implantation within the tissue annulus 90.

As shown in FIG. 7, a prosthesis 50 has been introduced into the heart and positioned against or otherwise adjacent the tissue annulus 90. In an exemplary embodiment, the prosthesis 50 may be an annuloplasty ring including an annular core covered by fabric that has sufficient structure to support the tissue annulus 90 while accommodating beating of the heart and the opening and closing of the leaflets. For example, the prosthesis 50 may include a core biased to a predetermined shape yet sufficiently flexible to accommodate normal movement of the leaflets. The prosthesis 50 may be "parachuted" over one or more sutures 52 or otherwise introduced into the tissue annulus 90 using known methods.

Also as shown in FIG. 7, a fastener tool may be used to deliver a plurality of clips or other fasteners through the prosthesis 50 and underlying tissue to substantially secure the prosthesis 50 to the tissue annulus 50, as shown in FIG. 8. Exemplary fasteners and tools that may be used are disclosed in application Ser. No. 10/681,700, filed Oct. 8, 2003, issued as U.S. Pat. No. 7,556,647; Ser. No. 11/004,445, filed Dec. 3, 2004, published as U.S. Publication No. 2006/0122634; and Ser. No. 12/115,543, filed May 5, 2008, published as U.S. Publication No. 2009/0036903. The entire disclosures of these references are expressly incorporated herein by reference. Alternatively, sutures or other fasteners (not shown) may be used to secure the prosthesis 50, e.g., in addition to or instead of clips.

If the tool has a substantially fixed reshaping element, the curved shape of the reshaping element may correspond to the predetermined shape of the prosthesis 50, e.g., to present the tissue for apposition against the prosthesis 50 while the fasteners are delivered. Alternatively, the reshaping element may be bent or otherwise manipulated to provide support for the tissue when the prosthesis 50 is pressed against the tissue and/or while fasteners are delivered through the prosthesis 50 into the adjacent tissue.

Once the prosthesis 50 is secured to the tissue, the reshaping element 20 may be removed from the tissue annulus 90 and the tool(s) 10 removed from the patient's body, leaving the prosthesis 50 as shown in FIG. 8. As shown in FIG. 8, the prosthesis 50 is an enclosed annular member. It will be appreciated that other prostheses, e.g., defining a "C" or other curved shape (not shown), may be provided that correspond to a tissue region to be supported.

Turning to FIG. 3, another exemplary embodiment of a remodeling tool 110 is shown that includes a handle 112 including a proximal end 114, a distal end 116, and a reshaping element 120 extending from the distal end 116 and terminating in a distal tip 122, e.g., a bulbous and/or rounded distal tip 122, similar to the previous embodiments. The handle 112 may be a substantially rigid elongate member, e.g., a hollow shaft, including a lumen or other passage 115 extending between the proximal and distal ends 114, 116 for receiving a core member 132, as described further below. The handle 112 may have a length sufficient to introduce the reshaping element 120 into a target tissue region, e.g., a tissue annulus, from outside the patient's body similar to the previous embodiments.

Optionally, the handle 112 may include one or more features to facilitate manipulation of the tool 110 during use. For example, the handle 112 may include knurling, ridges, and/or other raised or recessed features (not shown) along all or a portion of the handle 112 to facilitate gripping the tool 110. In addition or alternatively, the handle 112 may include an enlarged handpiece (not shown) on the proximal end 114, e.g., having an ergonomic or other shape to facilitate gripping the tool 110.

As shown in FIG. 3, an actuator 130 may be provided on the proximal end 114 of the handle 112 coupled to the reshaping element 120, e.g., for directing the reshaping element between different shapes or configurations. For example, the actuator 130 may be a wheel coupled to the core member 132 extending from the actuator 130 to the reshaping element 120, which may be rotated to pull, twist, or otherwise direct the core member 132 axially within the handle 112, as described further below. Alternatively, other actuators, e.g., dials, slider buttons, and the like (not shown) may be provided on a handpiece or otherwise on the proximal end 114 of the handle 112 for controlling the shape of the reshaping element 120.

With continued reference to FIG. 3, the reshaping element 120 may be directable between a first configuration, e.g., to facilitate direction through a tissue annulus, and a second configuration, e.g., to remodel tissue adjacent the tissue annulus. For example, the reshaping element 120 may include plurality of segments 124, e.g., cylinders, balls, coil segments, and the like, including respective passages therethrough that are aligned with one another to generally define an actuator passage 126 extending along the reshaping element 120. The core member 132, e.g., a solid or hollow wire, cable, and the like, may be slidably received in the actuator passage 126, e.g., such that the core member 132 extends from the actuator 130 on the proximal end 114 of the handle 112, through the lumen 115 of the handle 112 and the actuator passage 126 to the distal tip 122 of the reshaping element 120. The core member 132 may be fixed or otherwise coupled to the distal tip 122, e.g., by interference fit, bonding with adhesive, fusing, cooperating connectors (not shown), and the like.

In this configuration, the actuator 130 may be manipulated to direct the core member 132 axially relative to the distal tip 122, e.g., to direct the reshaping element 120 between a relaxed, first configuration (shown in phantom in FIG. 3) and a curved, second configuration. For example, initially, the actuator 130 may be provided in a first position in which the core member 132 is not subjected to a proximal force or substantial stress. Thus, the segments 124 of the reshaping element 120 may be relaxed and free to move somewhat relative to one another. In this relaxed configuration, the reshaping element 120 may be relative soft and flexible, which may facilitate introduction through a valve annulus without substantial risk of puncture or otherwise damaging leaflets or other tissue within the valve annulus.

When the actuator 130 is manipulated to direct the core member 132 proximally, a compressive force may be applied to the reshaping element 120, causing the segments 124 to engage one another. The shape and/or spacing of the segments 124 may be selected such that this engagement causes the reshaping element 120 to curve into a predetermined shape, e.g., a curvilinear shape defining a predetermined radius of curvature and/or arc length, similar to the previous embodiments. For example, end surfaces of the segments 124 may be non-orthogonal to a longitudinal axis of the reshaping element 120. For example, the end surfaces of adjacent segments 124 may be beveled or rounded such that, when the segments are compressed together, the end surfaces cause the segments 124 to rotate and/or align axially relative to one another to adopt a curvilinear shape. The angles defined by the end surfaces may extend laterally relative to the longitudinal axis, e.g., between forty five and ninety degrees (45-90°), or between sixty and eighty degrees (60-80°), to define a desired radius of curvature for the reshaping element 120. The angles of the end surfaces may be the same as one another to provide a uniform radius of curvature or may vary to provide a variable radius of curvature.

Optionally, the actuator 130 may be directed to two or more tensioned positions in which the reshaping element 120 is directed to different curved shapes, e.g., including a first larger radius curved configuration and a second smaller radius curved configuration, if desired, to provide multiple shapes with a single tool 110. Alternatively, similar to the previous embodiments, different tools may be provided that may be directed between relaxed configurations and curved configurations having different shapes such that an appropriate tool may be selected based on the anatomy encountered during a particular procedure.

Optionally, the reshaping element 120 may be biased to one of the relaxed or curved configurations. For example, a spring or other biasing element (not shown) may be provided within the handle 112 and/or actuator 130 for biasing the core member 132 to extend distally, thereby biasing the reshaping element 120 to the relaxed configuration. The actuator 130 may be selectively activated to pull the core member 132, thereby compressing the segments 124 and thereby directing the reshaping element 120 to the curved configuration. If desired, the actuator 130 may include a lock or other mechanism (not shown) that may be selectively activated to temporarily secure the reshaping element 120 in the curved configuration.

Alternatively, the tool 110 may be configured in an opposite manner. For example, the actuator 130 may be biased to pull the core member 132 and direct the reshaping element 120 to the curved configuration, with the actuator 130 activatable to push the core member 132 distally and thereby direct the reshaping element 120 to the relaxed configuration. Optionally, the actuator 130 may include a lock to temporarily secure the reshaping element 120 in the relaxed configuration, if desired.

The tool 110 of FIG. 3 may be used similar to the previous embodiments, e.g., to remodel tissue within a mitral valve annulus or other tissue annulus, e.g., during an annuloplasty procedure. For example, with reference to the anatomy shown in FIG. 5, with the reshaping element 120 in its relaxed configuration (shown in phantom in FIG. 3), the tool 110 may be introduced into a patient's body until the reshaping element 120 passes through the tissue annulus 90 and behind leaflets 92. The distal tip 122 may facilitate directing the reshaping element 120 through the leaflets 92 without substantial risk of damaging the leaflets 92 or other tissue structures.

The actuator 130 may then be activated to direct the reshaping element 120 to its curved configuration, e.g., extending between mitral valve structures and the ventricular wall 94. The tool 110 may then be manipulated to lift or otherwise manipulate tissue within valve annulus 90 while a prosthesis is introduced and secured to the valve annulus 90, such as the prosthesis 50 shown in FIGS. 7-8. After the prosthesis has been secured, the reshaping element 120 may be returned to its relaxed configuration, and the tool 110 removed from the patient's body.

Figure 4A:
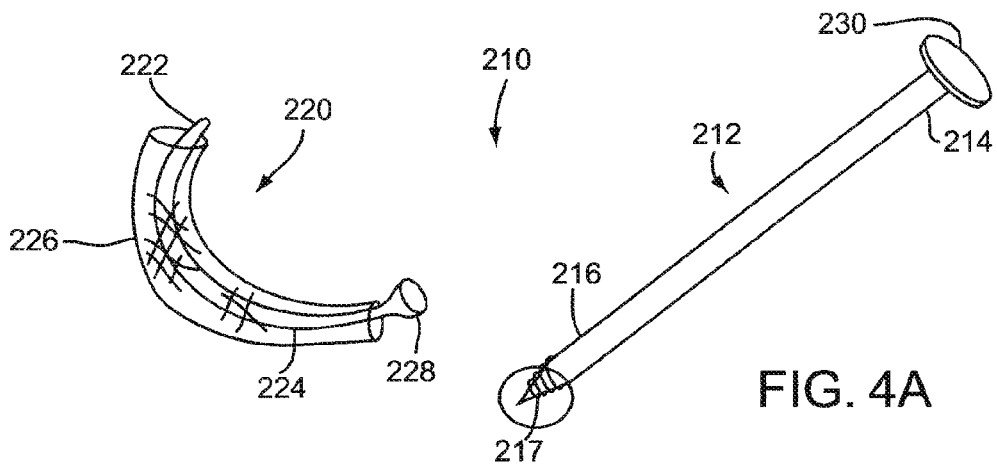
FIG. 4A is a perspective view of a handle of yet another exemplary embodiment of a tool and a first exemplary embodiment of a reshaping element that may be releasably attached to the handle.

Turning to FIG. 4A, another exemplary embodiment of a tool 210 for remodeling tissue is shown that includes an elongate handle 212 and a reshaping element 220, which may be generally similar to the previous embodiments. However, unlike the previous embodiments, the reshaping element 220 is detachable or releasable from the handle 212, e.g., to provide an implant for supporting or otherwise treating a tissue annulus.

Generally, similar to the previous embodiments, the handle 212 is a substantially rigid elongate member, e.g., a hollow shaft, including a proximal end 214 and a distal end 216, and having a length sufficient to introduce the reshaping element 220 into a target tissue region, e.g., a valve or other tissue annulus, from outside the patient's body. Unlike the previous embodiments, one or more connectors 217 may be provided on the distal end 216 for releasably engaging the reshaping element 220. One or more actuators 230 may be provided on the proximal end 214 of the handle 212, e.g., to engage or release the connector(s) 217, for example, to secure or release the reshaping element 220 relative to the handle 212 and/or to direct the reshaping element 220 between different shapes or configurations, as described further below.

For example, in the embodiment shown in FIG. 4A, the reshaping element 220 includes a substantially rigid or malleable shaft 224, e.g., similar to the reshaping elements 20, 20', 20" shown in FIGS. 1 and 2 and described further elsewhere herein. As shown, the reshaping element 220 includes a bulbous and/or atraumatic distal tip 222 on one end and one or more connectors 228 on the opposite end.

Optionally, if the reshaping element 220 is intended for implantation, a fabric covering 226 may be provided over at least a portion of the shaft 224, e.g., to facilitate tissue ingrowth and/or enhance biocompatibility of the reshaping element 220. For example, the fabric covering 226 may extend from connectors 228 to the distal tip 222, either of which may be covered with fabric or exposed, as desired. In addition or alternatively, the shaft 224 may be formed from biocompatible material, e.g., including a thrombolytic or other coating, if desired.

In an exemplary embodiment, the connector(s) 217 on the handle 212 may include one or more collets or graspers and the connector(s) 228 on the reshaping element 220 may include a lip or other feature that may be selectively captured or engaged by the grasper(s). In this embodiment, the actuator 230 may include a dial, button, or other feature that may be depressed or otherwise activated to open the graspers, e.g., to release or receive the lip on the reshaping element 220. When the button is released, the graspers may be biased to a closed position, thereby engaging the lip and securing the reshaping element 220 relative to the handle 212. Alternatively, the connectors 217, 228 may simply be mating threads that may be engaged together or disengaged from one another by rotating the handle 212 relative to the reshaping element 220. In a further alternative, the connector(s) 217 may be carried by a core member (not shown) extending through the handle 212 that is coupled to the actuator 230 such that the core member may be manipulated to engage or disengage the connector(s) 217 with mating connector(s) 228 on the reshaping element 220.

Optionally, a plurality of reshaping elements (not shown) may be provided having different shapes and/or sizes. During use, a reshaping element having a desired configuration, such as reshaping element 220, may be selected and attached to the handle 212 using the connectors 217, 228. A set of reshaping elements may be useful if each reshaping element has a substantially fixed shape or is malleable to provide greater flexibility to a user.

During use (with reference again to the anatomy shown in FIG. 5), a desired reshaping element 220 may be secured to the handle 212 to provide a tool 210. The tool 210 may be introduced into a patient's body, e.g., by directing the distal tip 222 and the reshaping element 220 through and behind valve leaflets 92 of a mitral valve annulus 90. The tool 210 may then be manipulated to lift or otherwise remodel tissue surrounding the valve annulus 90, similar to the previous embodiments. One or more fasteners, e.g., clips and/or sutures, as described above, may be directed through the tissue and through at least a portion of the reshaping element 220, e.g., to secure the reshaping element 220 relative to the valve annulus 90. For example, a plurality of fasteners may be directed through the fabric covering 226 of the reshaping element 220 and/or around the shaft 224 along the length of the reshaping element 220 to secure the reshaping element 220 to the adjacent tissue.

Once the reshaping element 220 is sufficiently secured, the actuator 230 may be activated to release the reshaping element 220 from the handle 212, whereupon the handle 212 may be removed, leaving the reshaping element 220 indefinitely within the valve annulus 90 as an implant to support the valve annulus 90, similar to an annuloplasty ring. Optionally, one or more additional reshaping elements (not shown) may be introduced and secured to the valve annulus 90, e.g., one under each of the valve leaflets 92, in a similar manner, if desired.

Figure 4B:
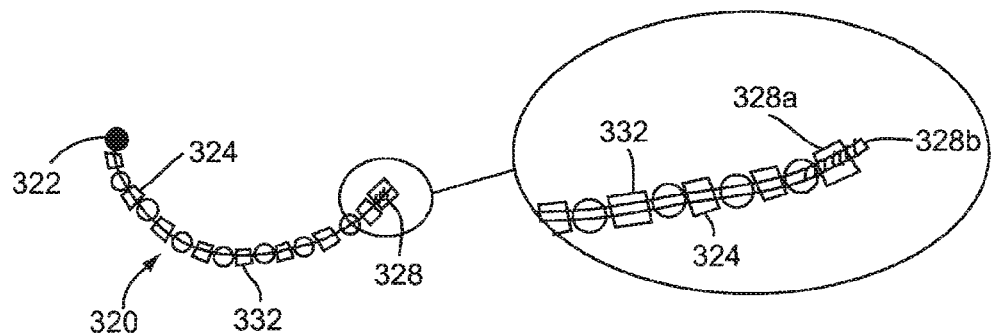
FIG. 4B is a perspective view of a second exemplary embodiment of a reshaping element that may be releasably attached to the handle of FIG. 4A.

Turning to FIGS. 4B and 4B1, an alternative embodiment of a detachable reshaping element 320 is shown that includes one or more connectors 328 for releasably attaching the reshaping element 320 to a handle, such as handle 212 shown in FIG. 4A. In addition, the reshaping element 320 is adjustable between one or more shapes, e.g., between a relaxed, first configuration and a curved, second configuration, which may be similar to the reshaping element 120 of the tool 110 of FIG. 3. For example, as shown in FIG. 4B, the reshaping element 320 includes a plurality of segments 324, e.g., cylinders, balls, coil segments, and the like, that are slidably received over a core member 332, e.g., a solid or hollow wire, rod, and the like. The core member 332 may be fixed or otherwise coupled on one end to a distal tip 322 of the reshaping element 320 and may include a connector 328b on the other end that cooperates with a locking element 328a.

Optionally, the reshaping element 320 may include a fabric covering (not shown) at least partially covering the segments 324 and/or core member 332. For example, a layer of fabric may be provided over the entire reshaping element 320, e.g., from the distal tip 322 to the locking element 328a, with the connector 328b extending from the fabric covering.

In this embodiment (with reference generally to the handle 212 shown in FIG. 4A), the handle 212 may include one or more connectors 217 on the distal end 216 that may releasably engage the connector 328b and/or the locking element 328a. For example, the actuator 230 may be coupled to a shaft or other actuator member (not shown) that extends from the proximal end 214 to the distal end 216 of the handle 12. The actuator member may include a connector 217, e.g., a grasper, threads, and the like, that may selectively engage the connector 328b on the core member 332 of the reshaping element 320.

For example, during use, the reshaping element 320 may be attached to the handle 212, e.g. by engaging the connector 328b on the core member 332 to the connector 217 on the handle 212. Thus, the core member 332 in the reshaping element 320 may be coupled to the actuator member within the handle 212, thereby coupling the core member 332 to the actuator 230. With the reshaping element 320 attached to the handle 212, the locking element 328a may abut or be disposed immediately adjacent the distal end 216 of the handle 212, e.g., to prevent excessive movement of the reshaping element 320 relative to the handle 212. Alternatively, the locking element 328a and/or distal end 216 of the handle 212 may include one or more connectors (not shown) for securing the locking element 328a directly to the distal end 216 of the handle 212.

Thus, with the connectors 217, 328b engaged, the segments 324 of the reshaping element 320 may be free to move, e.g., thereby providing the reshaping element 320 in a floppy or relaxed configuration, which may facilitate introduction into a tissue annulus, similar to the previous embodiments. In addition or alternatively, when the connectors 217, 328b are engaged, the actuator 230 may apply a minimal proximal tension on the core member 332, thereby pulling the segments 324 proximally to abut one another to prevent excessive movement of the reshaping element 320 without causing the reshaping element to adopt a fixed, rigid shape.

Once the reshaping element 320 is introduced into a tissue annulus or otherwise positioned as desired, the actuator 230 on the handle 212 may be activated to direct the actuator member proximally. The actuator member consequently pulls the core member 332 within the reshaping element 320, thereby causing the segments 326 to compress against one another and direct the reshaping element 320 to a curved, relatively rigid configuration. The locking element 328a may prevent the core member 332 from subsequently moving distally to release the reshaping element 320 from the curved configuration. For example, the locking element 328a may include one or more internal ratchets or other detents (not shown) that may engage the core member 332 adjacent the connector 328a. Thus, the tension applied to the core member 332 by the actuator 230 may be indefinitely stored in the core member 332 to secure the reshaping element 320 in the curved configuration. Alternatively, the locking element 328a may include internal threads or other features (not shown) that may cooperate with mating threads or other features (also not shown) on the core member 332 adjacent the connector 328b. These features may allow tension to be applied to the core member 332, e.g., by rotating the core member 332 in a first direction relative to the locking element 328a, yet allow the tension to be released if desired, e.g., by rotating the core member 332 in a second opposite direction. In this alternative, the core member 332 may be fixed axially relative to the distal tip 322 of the reshaping element 320 but rotatable relative to the distal tip 322.

Once sufficient tension is applied to the core member 332 to direct the reshaping element 320 to the curved configuration, the reshaping element 320 may be manipulated within the tissue annulus and/or secured to tissue adjacent to the tissue annulus, e.g., using one or more fasteners, similar to the previous embodiments. The reshaping element 320 may then be released from the handle 212, e.g., by manipulating the actuator 230 to disengage the connectors 217, 328b. The handle 212 may then be removed, leaving the reshaping element 320 implanted within the tissue annulus. Optionally, if desired, after implantation, the reshaping element 320 may be accessed, e.g., to adjust the shape of the reshaping element 320. The connector 328b may be reengaged and then the core member 332 may be directed axially relative to the locking element 328a, e.g., to adjust the radius and/or shape of the reshaping element 320.

Figure 4C:
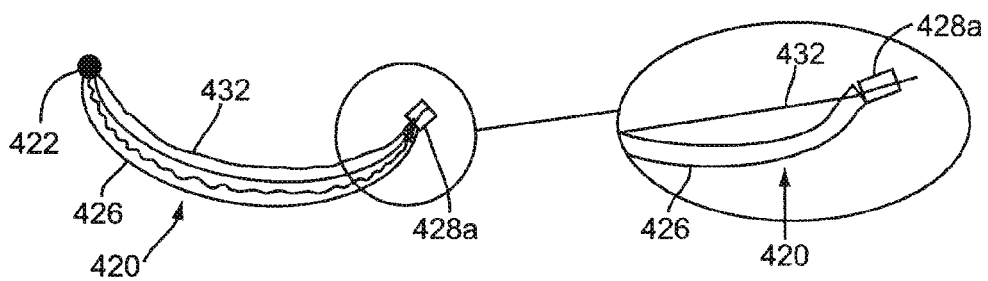
FIG. 4C is a perspective view of a third exemplary embodiment of a reshaping element that may be releasably attached to the handle of FIG. 4A.

Turning to FIGS. 4C and 4C1, another exemplary embodiment of an adjustable, detachable, and/or implantable reshaping element 420 is shown. Similar to the previous embodiments, the reshaping element 420 includes one or more connectors 428 for releasably attaching the reshaping element 420 to a handle, such as handle 212 shown in FIG. 4A. The reshaping element 420 includes a roll of fabric 426 that extends between a distal tip 422 and a locking element 428a of the reshaping element 420. Optionally, a core, shaft or other elongate member (not shown) may be provided within the fabric roll 426, e.g., to provide a desired shape and/or stiffness to the fabric roll 426. Alternatively, a fabric covering may be provided around a core member having a desired rigidity to provide an adjustable reshaping element.

In addition, the reshaping element 420 includes an actuator member 432, e.g., a solid or hollow wire, rod, suture, and the like, that is coupled on one end to the distal tip 422 of the reshaping element 420 and to the locking element 428a. For example, the locking element 428a may include a passage (not shown) therethrough that includes one or more ratchets, detents, threads, and/or other features, similar to the previous embodiment, that allow the actuator member 432 to be pulled proximally through the locking element 428a, yet prevent undesired subsequent distal movement, to maintain an applied tension on the actuator member 432.

The actuator member 432 may also be slidably secured to the fabric roll 426 at one or more locations between the distal tip 422 and locking element 428a. For example, during assembly, the actuator member 432 may be directed through the fabric roll 426 to pick up one or more threads of the fabric roll 426 at a plurality of intermediate locations between the distal tip 422 and locking element 428a. Alternatively, if the reshaping element 420 includes a core member within the fabric roll 426, the actuator member 432 may be slidably received in one or more pockets, apertures, or passages (not shown) in the core member such that actuator member 432 is free to slide axially relative to the core member.

The actuator member 432 may include one or more connectors (not shown) adjacent the locking element 428a, e.g., for releasably attaching the reshaping element 420 to a handle, e.g., that may be engaged with the connector(s) 217 on the handle 212 shown in FIG. 4A. Alternatively, the actuator member 432 may extend through a passage in the handle 212 and be coupled to the actuator 230 during manufacturing and/or assembly. In this alternative, when it is desired to release the reshaping element 420 from the handle 212, the actuator member 432 may be cut, severed, or broken at a location beyond the locking element 428a.

During use, the reshaping element 420 may be attached to the handle 212, e.g. by engaging a connector (not shown) on the actuator member 432 to the connector 217 on the handle 212 or by coupling the actuator member 432 directly between the actuator 230 on the handle 212 and the distal tip 422, e.g., during assembly. Thus, the actuator member 432 of the reshaping element 420 may be coupled to the actuator 230 on the handle 212. With the reshaping element 420 attached to the handle 212, the locking element 428a may abut or be disposed immediately adjacent the distal end 216 of the handle 212, e.g., to prevent excessive movement of the reshaping element 420 relative to the handle 212. Alternatively, the locking element 428a and/or distal end 216 of the handle 212 may include one or more connectors (not shown) for securing the locking element 428a directly to the distal end 216 of the handle 212.

Thus, with the reshaping element 420 attached to the handle 212, the distal tip 422 may be free to move, e.g., thereby providing the reshaping element 420 in a floppy or relaxed configuration, which may facilitate introduction into a tissue annulus, similar to the previous embodiments.

Once the reshaping element 420 is introduced into a tissue annulus or otherwise positioned as desired, the actuator 230 on the handle 212 may be activated to direct the actuator member 432 proximally. Because the actuator member 432 is attached to outer surface of the fabric roll 426, the tension on the actuator member 432 causes the fabric roll 426 to bend into a curved configuration, as shown in FIG. 4C. The locking element 428a may prevent the actuator member 432 from subsequently moving distally to release the reshaping element 420 from the curved configuration. Thus, the tension applied to the actuator member 432 by the actuator 230 may be indefinitely stored in the actuator member 432 to maintain the reshaping element 420 in the curved configuration. Alternatively, the locking element 428a may include internal threads or other features (not shown) that may cooperate with mating threads or other features (also not shown) on the actuator member 432. These features may allow tension to be applied to and/or released from the actuator member 432, similar to the previous embodiments.

Once sufficient tension is applied to the actuator member 432 to direct the reshaping element 420 to the curved configuration, the reshaping element 420 may be manipulated within the tissue annulus and/or secured to tissue adjacent to the tissue annulus, e.g., using one or more fasteners, similar to the previous embodiments. The reshaping element 420 may then be released from the handle 212, e.g., by manipulating the actuator 230 to disengage the connector(s) 217. Alternatively, if the actuator member 432 is coupled directly to the actuator 230, the actuator member 432 may be cut or otherwise severed adjacent the locking element 428a. For example, the handle 212 may include a release button to allow excess length of the actuator member 432 to be exposed and cut. Alternatively, the actuator member 432 may include a weakened region, e.g., within the handle 212 or otherwise adjacent the locking element 428a that may be severed by applying a predetermined axial tension on the actuator member 432 greater than the tension applied to direct the reshaping element 420 to the curved configuration. The handle 212 (and any excess actuator member length) may then be removed, leaving the reshaping element 420 implanted within the tissue annulus.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A system for treating a cardiac valve including a tissue annulus and leaflets, the system comprising:
   a remodeling tool including a handle and a reshaping element extending from a distal end of the handle, the reshaping element having a shape to pass between leaflets of a cardiac valve and remodel tissue adjacent a tissue annulus of the cardiac valve; and
   a prosthesis configured for securing to the tissue, wherein the reshaping element is configured to be spaced apart from the prosthesis and to provide support for the tissue when the prosthesis is pressed against the tissue, wherein the system is configured such that the reshaping element and the prosthesis are delivered to the cardiac valve apart from one another.

2. The system of claim 1, wherein the system is configured to locate the reshaping element and the prosthesis at opposite sides of a thickness of the tissue annulus.

3. The system of claim 1, further comprising:
   a plurality of fasteners receivable through tissue adjacent the tissue annulus for securing the prosthesis to the tissue annulus.

4. The system of claim 3, further comprising:
   a tool for delivering the fasteners into tissue adjacent the tissue annulus.

5. The system of claim 1, wherein the handle is rigid and the reshaping element is malleable.

6. The system of claim 1, wherein extension of the reshaping element from the handle defines a curve in a plane that intersects a longitudinal axis of the handle.

7. The system of claim 6, wherein an angle in the range of 30°-60° is defined by the longitudinal axis and the plane.

8. The system of claim 6, wherein a shape of the reshaping element is fixed.

9. The system of claim 1, wherein the reshaping element is configured to be directable to a curved configuration defining a radius of curvature to extend partially around the tissue annulus.

10. The system of claim 9, wherein the remodeling tool further includes an actuator adjacent a proximal end of the handle and coupled to the reshaping element for directing the reshaping element from a relaxed configuration that facilitates introduction between the leaflets to the curved configuration.

11. A method for treating a cardiac valve within a patient's heart, the method comprising:
    delivering the prosthesis to a tissue annulus of the cardiac valve;
    introducing a reshaping element of a remodeling tool between leaflets of the cardiac valve, the reshaping element extending from a distal end of a handle of the remodeling tool;
    remodeling tissue adjacent the tissue annulus to a desired remodeled state with the reshaping element;
    securing the prosthesis to the tissue annulus while the reshaping element supports the tissue annulus in the remodeled state; and
    removing the reshaping element from the cardiac valve,
    wherein the prosthesis is delivered to the tissue annulus apart from the reshaping element.

12. The method of claim 11, wherein the step of securing the prosthesis includes locating the prosthesis at one side of a thickness of the tissue annulus and the reshaping element at an opposite side of the thickness of tissue annulus.

13. The method of claim 11, wherein the step of remodeling tissue includes threading the reshaping element behind the leaflets and chordae tendinae of the cardiac valve.

14. The method of claim 11, wherein the step of remodeling tissue includes lifting the tissue annulus.

15. The method of claim 11, wherein the step of securing a prosthesis includes applying a pressing force on to the tissue annulus via the prosthesis in a first direction and applying a lifting force on to the tissue annulus via the reshaping element in a second direction opposite the first direction.

16. The method of claim 11, wherein the reshaping element is introduced between the leaflets in a first configuration, and wherein the step of remodeling tissue adjacent the tissue annulus includes:
    directing the reshaping element to a second curved configuration below the tissue annulus; and
    lifting tissue adjacent the tissue annulus using the reshaping element in the second curved configuration.

17. The method of claim 11, wherein the cardiac valve is a mitral valve, and further wherein the step of introducing the reshaping element includes inserting the reshaping element between structures of the mitral valve annulus and a ventricular wall of the heart.

18. The method of claim 11, wherein the prosthesis comprises one of an annular shape and a "C" shape.

19. The method of claim 11, further comprising adjusting the shape of the reshaping element until the desired remodeled shape of the portion of the tissue adjacent the tissue annulus of the cardiac valve is achieved.

20. The method of claim 19 wherein the step of adjusting the shape of the reshaping element includes adjusting the curvature of the reshaping element.

21. The method of claim 19 wherein the step of adjusting the shape of the reshaping element includes detaching the reshaping element having a first shape from the handle and coupling a different shaping element having a second shape which is different from the first shape.

22. A method for treating a cardiac valve within a patient's heart, the method comprising:
introducing a reshaping element of a remodeling tool between leaflets of the cardiac valve, the reshaping element extending from a distal end of a handle of the remodeling tool;
remodeling tissue adjacent a tissue annulus of the cardiac valve to a remodeled state with the reshaping element, wherein the reshaping element is threaded behind the leaflets and chordae tendinae of the cardiac valve;
securing a prosthesis to the tissue annulus while the reshaping element supports the tissue annulus in the remodeled state; and
removing the reshaping element from the cardiac valve.

* * * * *